United States Patent [19]

Balteau et al.

[11] Patent Number: 5,431,496
[45] Date of Patent: Jul. 11, 1995

[54] MULTIPLE CHAMBER CONTAINER

[75] Inventors: Patrick Balteau, St Denis; Dirk Faict, Assenede; Francesco Peluso, Heverlee, all of Belgium

[73] Assignee: Baxter International Inc., Deerfield, Ill.

[21] Appl. No.: 295,363

[22] Filed: Aug. 24, 1994

Related U.S. Application Data

[63] Continuation of Ser. No. 6,339, Jan. 19, 1993, abandoned.

[51] Int. Cl.6 .............................................. B65D 30/22
[52] U.S. Cl. ...................................... 383/38; 206/219; 604/410
[58] Field of Search .................. 383/38, 41, 904, 906; 206/219; 604/410

[56] References Cited

U.S. PATENT DOCUMENTS

| | | |
|---|---|---|
| 3,304,977 | 2/1967 | Hammons ...................... 383/38 X |
| 3,542,032 | 11/1970 | Spencer, Jr. .................... 206/219 X |
| 4,396,382 | 8/1983 | Goldhaber . |
| 4,396,383 | 8/1983 | Hart . |
| 4,458,733 | 7/1984 | Lyons . |
| 4,465,438 | 8/1984 | Richmond et al. . |
| 4,467,588 | 8/1984 | Carveth . |
| 4,484,920 | 11/1984 | Kaufman et al. . |
| 4,529,102 | 7/1985 | Quinn et al. .................... 604/410 X |
| 4,608,043 | 8/1986 | Larkin .............................. 206/219 X |
| 4,630,727 | 12/1986 | Feriani et al. . |
| 4,997,083 | 3/1991 | Loretti et al. ...................... 383/38 X |
| 5,061,236 | 10/1991 | Sutherland et al. ............ 604/410 X |
| 5,261,532 | 11/1993 | Fauci ................................. 383/38 X |

FOREIGN PATENT DOCUMENTS

| | | | |
|---|---|---|---|
| 0132632 | 2/1985 | European Pat. Off. ............ 206/219 |
| 3238649A1 | 4/1984 | Germany . |
| 582101 | 11/1976 | Switzerland ........................ 206/219 |
| 0458538 | 12/1936 | United Kingdom .................. 383/38 |

Primary Examiner—Jes F. Pascua
Attorney, Agent, or Firm—Thomas S. Borecki; Charles R. Mattenson; Robert M. Barrett

[57] ABSTRACT

A multiple chamber container for mixing and administering a plurality of products. The container has at least two chambers separated by a seal line. A frangible connector is situated between the two chambers for mixing the products contained within the chambers as desired. Each chamber has at least one port for filling of product into the chamber. The ports are located on the same exterior side of the container such that the chambers can be filled without folding the bag and by using existing filling equipment.

13 Claims, 2 Drawing Sheets

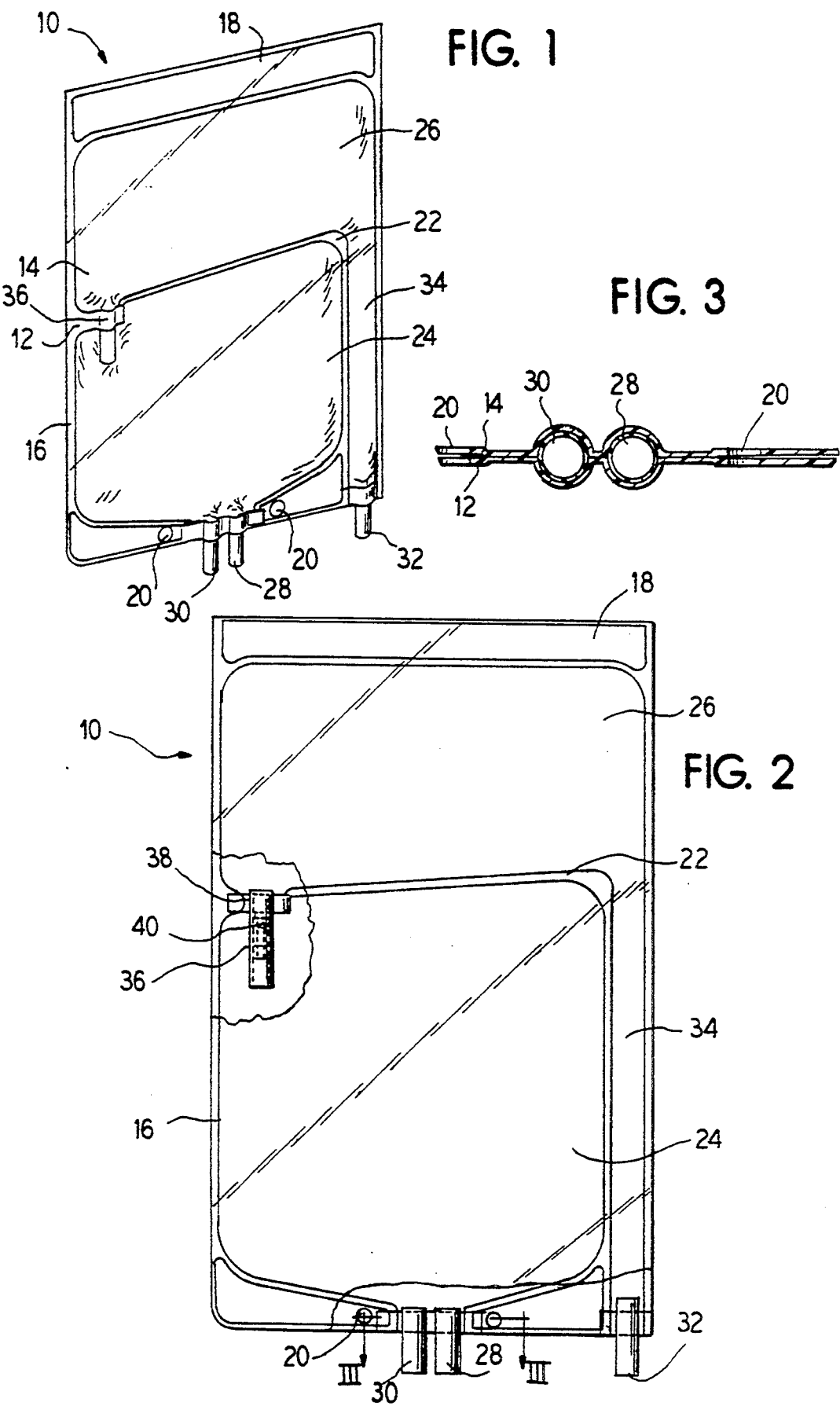

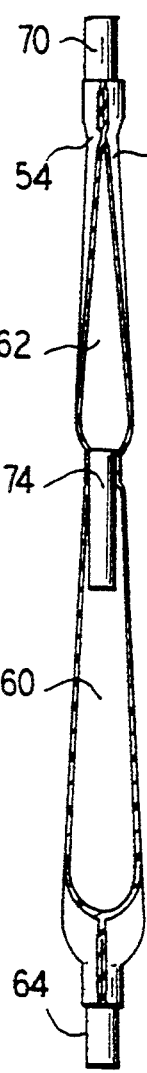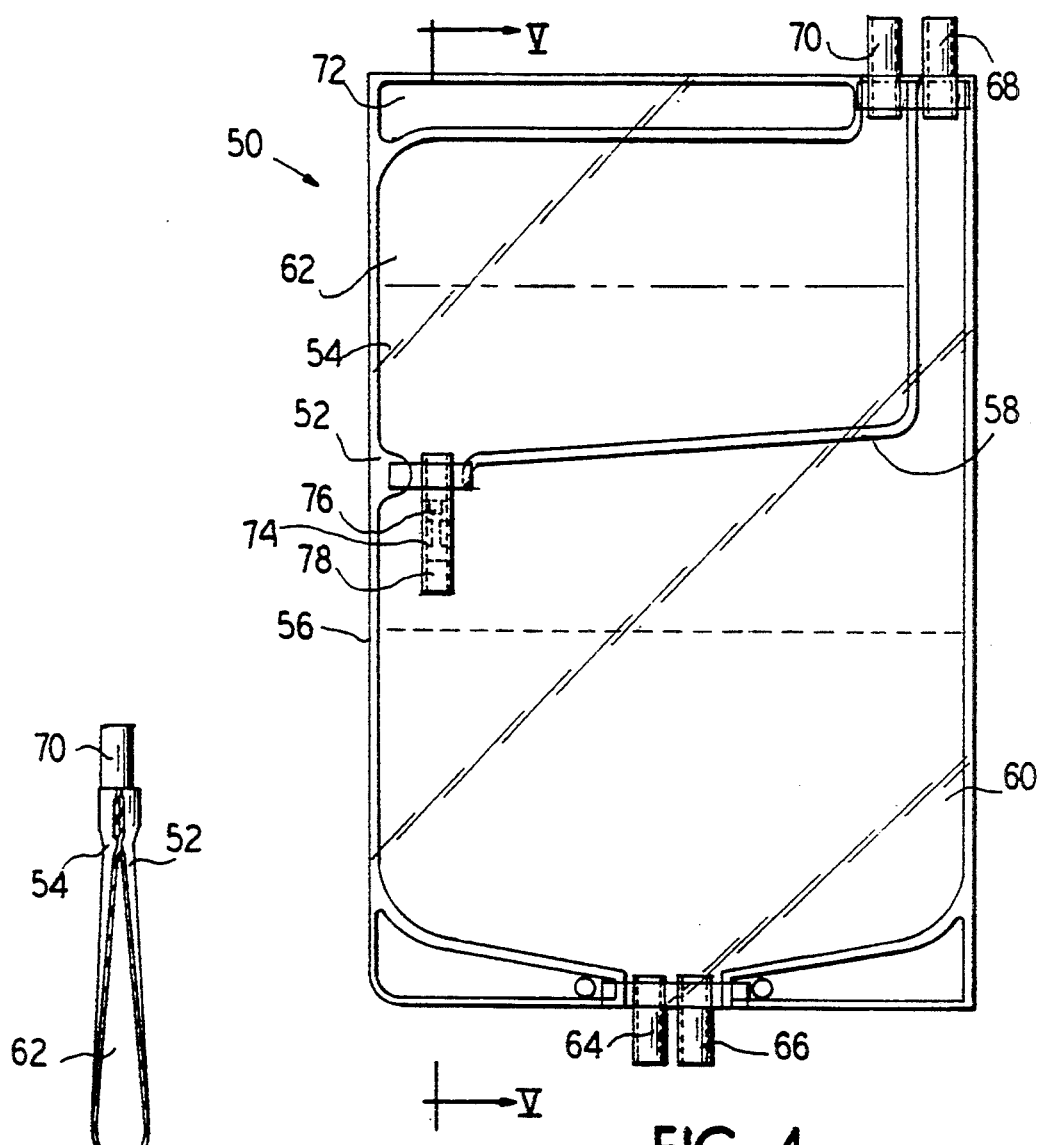
FIG. 4
FIG. 5

MULTIPLE CHAMBER CONTAINER

This application is a continuation of application Ser. No. 08/006,339, filed Jan. 19, 1993, now abandoned.

BACKGROUND OF THE INVENTION

The present invention generally relates to a multiple chamber container. More specifically, the invention relates to a flexible bag for storing a medical product having two or more chambers each containing a solution or other product.

It is known to house a number of different products in flexible containers. For example, in the medical field, it is known to house enteral, intravenous, and peritoneal solutions in flexible containers. Generally, medical solutions can be administered directly to a patient through a port that provides fluid communication to an interior of the container.

Often, one or more solutions or ingredients are combined to form a solution to be administered to the patient. Combined medical solutions may be typically unstable. Degradation of mixed solutions can occur during the manufacturing process, for example during sterilization. Likewise during long term storage such products may degrade or suffer reduced efficacy. For example, amino acid and dextrose may be combined to form a parenteral solution for intravenous administration to a patient. If amino acid and dextrose are combined in a single container and stored, discoloration often takes place. Other examples of non-compatible solutions include: bicarbonate-dextrose; amino acid polymers-dextrose; bicarbonate-dextrose polymers; and amino acid polymers-dextrose polymers.

As a result, in some situations, amino acids and dextrose are sold separately. If a combined amino acid and dextrose solution is prescribed, the amino acid solution and dextrose solution must be combined from two separate containers. The transfer of fluid from one container to another can be time consuming and requires the use of transfer tubing and/or connectors between the two separate containers. Additional risks for fluid contamination is also present using such procedures.

Containers, therefore, have been developed to reduce the risk of contamination and to provide a more simple and less time consuming procedure for combining at least two solutions. For example, containers having more than one chamber for storing a respective number of solutions prior to mixing are known. The chambers of these containers are segregated from each other, but selective communication is possible through the use of a frangible seal or closure between the chambers which may be opened from outside the container by manipulating the walls of the container.

An example of such a container is set forth in U.S. Pat. No. 4,465,488 to Richmond et al. As disclosed in the '488 patent, an interior of a flexible, plastic container is separated into two chambers by a heat seal. A connecting port between the two chambers is sealed by a frangible seal. When the seal is broken, the two chambers are in fluid communication through the port.

Another multiple chamber container is described in U.S. Pat. No. 4,396,383 to Hart. As described in the disclosure of Hart, a container having a two-chamber construction provides for passive mixing of two solutions having different specific gravities into a single homogenous solution in a closed environment. The container includes fill ports at opposite ends of the container for filling the respective chambers with solutions. The chambers, however, may not be filled simultaneously without folding the bag or without specially designed filling equipment which can fill the chambers from opposite sides.

A need, therefore, exists for an improved multiple chamber container.

SUMMARY OF THE INVENTION

The present invention provides an improved multiple chamber container for housing and dispensing a plurality of products. The container is constructed such that the products may be filled and stored in two separate chambers within the container. A frangible valve between the chambers, when broken, allows the products in the two chambers to be mixed to form a single solution that can be dispensed and administered to a patient. The ports to the chambers are located on the same exterior side of the container such that the chambers may be filled simultaneously without folding the bag and by using currently available filling equipment.

In an embodiment, the present invention provides a container for mixing two products. The container includes on an interior thereof dividing means that define a first chamber and a second chamber. The first chamber may be filled with a first product and the second chamber may be filled with a second product. A frangible valve between the chambers provides selective communication between the chambers. A first port connected to the first chamber on one of the exterior sides of the container can be used for filling the first chamber. A second port connected to the second chamber is located on the same exterior side of the container as the first port for filling the second chamber.

In an embodiment, the first port and the second port are on the exterior side at the base of the container.

In an embodiment, the first and the second port are on the exterior side at the top of the container.

In an embodiment, an additional port is provided for providing means for adding additional product to the chambers or for dispensing product from the chambers.

The present invention also provides a method for filling and mixing products in a container. The method comprises the steps of filling a first chamber with a first solution through a first port and filling a second chamber with a second solution through a second port. The first port and the second port are located on the same exterior side of the container.

In an embodiment, the method further comprises the step of breaking a frangible connector between the first chamber and the second chamber and mixing the products contained within the chambers.

Although the present invention can be used to store any variety of products, the container is especially adaptable for storing medical solutions, especially peritoneal dialysis solutions.

An advantage of the present invention is that it provides a container for filling and mixing two or more products without folding the container.

A further advantage of the present invention is that it provides a method for filling and mixing two or more products without specially designed filling equipment.

Furthermore, an advantage of the present invention is that it provides a container for filling and mixing two or more products prior to administration of the mixed products to a patient.

Moreover, an advantage of the present invention is that it provides a container for filling and mixing two or more products without product degradation.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of an embodiment of a multiple chamber container of the present invention.

FIG. 2 illustrates a front elevational view of the embodiment of the multiple chamber container shown in FIG. 1.

FIG. 3 illustrates a cross-sectional view of a portion of the multiple chamber container taken generally along the lines III—III in FIG. 2.

FIG. 4 illustrates a front elevational view of another embodiment of a multiple chamber container of the present invention.

FIG. 5 illustrates a cross-sectional view of the multiple chamber container taken generally along the lines V—V in FIG. 4.

DETAILED DESCRIPTION OF THE PRESENTLY PREFERRED EMBODIMENTS

In accordance with the present invention, a multiple chamber container 10 is provided for housing and mixing at least two solutions or products into a single mixture prior to administration to a patient.

Referring to FIGS. 1-3, wherein like numerals designate like components, a container 10 constructed pursuant to the present invention is illustrated. The container 10 is defined, at least in part, by walls 12 and 14. Container walls 12 and 14 may be formed from flexible plastic sheets joined by means such as a heat seal 16 about the periphery of the walls 12 and 14. If desired, however, the walls 12 and 14 can be formed from a single web of film that is folded and sealed along three sides to create the container 10.

In the illustrated embodiment, a wider portion of the heat seal 16 is formed at an end of the container 10 to form a flange 18. The flange 18 generally can have a stronger heat seal to assist the container 10 in keeping its shape when suspended.

Likewise, in the illustrated embodiment, openings 20 are provided within the heat seal 16 at the lower end of the container 10. The openings 20 provide means for hanging the container 10 and holding the container 10 in a stable position during the filling process.

The interior of the container is divided by a heat seal 22 into a lower chamber 24 and an upper chamber 26. The seal 22 and the walls 12 and 14 of the container 10 define the boundaries of the lower chamber 24 and the upper chamber 26.

A fill port 28 is located at the lower end of the lower chamber 24 to provide a means for adding product to the chamber 24. In addition, in the illustrated embodiment, a medication port 30 is located adjacent the fill port 28 of the lower chamber 24. It should be appreciated, that although a medication port 30 is provided, the container 10 can be constructed without the port or with additional ports.

A second fill port 32 is located at the lower end of the container 10 at the lower end of the upper chamber 26. In this regard, the upper chamber 26 includes a channel or neck portion 34 which provides communication between the fill port 32 and the upper chamber 26.

In order to provide means for allowing the fluid contained within the lower and upper chambers 24 and 26 to be mixed, a frangible connector 36 is provided. The frangible connector 36 is located between the lower chamber 24 and the upper chamber 26 to provide communication between the chambers 24 and 26. When the frangible connector 36 is broken by a user, such as medical personnel, fluid communication is established between the two chambers. A number of possible frangible connector structures can be used. U.S. Pat. No. 4,465,488, the disclosure of which is incorporated herein by reference, discloses one such possible structure.

The container 10 may, therefore, be constructed such that the seal 22 defines a top portion of the lower chamber 24 which substantially meets with a lower portion of the upper chamber 26. The seal 22 further extends perpendicularly to the side of the container along a side of the lower chamber 24 and the fluid channel 34 of the upper chamber 26.

To mix the solutions of the chambers 24 and 26, the frangible connector 36 situated between the chambers 24 and 26 is manipulated until the frangible connector 36 is selectively opened by the user who forcibly breaks the frangible connector 36. Fluid communication between the chambers will then be established.

In the preferred embodiment illustrated, the frangible connector 36 is situated between the top portion of the lower chamber 24 and the lower portion of the upper chamber 26. The frangible connector 36, as illustrated in FIG. 2, includes at least one tube 38 with a break away valve 40 therein. The break away valve 40 may be mounted within the plastic tube 38 as is well known to provide communication between products in the chambers 24 and 26. However, other constructions of valves within the tube 38 of the frangible connector 36 may also be implemented in the container 10 of the present invention.

To mix the solution within the chambers 24 and 26, the frangible connector 36 is broken. The transfer of product is thereby initiated from the upper chamber 26 to the lower chamber 24. Typically, a higher specific gravity solution is stored in the upper chamber 26 than the solution stored in the lower chamber 24. However, one of the chambers may include a "dry" product for mixing with a solution. Upon breaking of the frangible connector 36, the heavier solution from the upper chamber 26 flows into the lower chamber 24 through the valve 40 of the frangible connector 36 with the container 10 suspended such that the chamber 26 is substantially above the chamber 24.

As a result, the solution level in the upper chamber 26 decreases as the product level in the lower chamber 24 increases. Once the product from the upper chamber 26 is depleted therefrom and added to the lower chamber 24, the mixed solution can be dispensed through the port 28.

The illustrated embodiment of FIGS. 1 and 2 illustrates three ports. Two ports 28 and 30 may be connected to the lower chamber 24, and a single port 32 is connected to the channel 34 of the upper chamber 26. The additional port 30 connected to the lower chamber 24 may be used as a port for addition of further product or solution or as a supplemental administration port.

When mixing of products has been completed, a mixture of the two solutions is located in the lower chamber 24. Typically, the volume ratio between the lower chamber 24 and the upper chamber 26 is at least ⅔.

An alternative embodiment of a multiple chamber container 50 is illustrated in FIGS. 4 and 5. The container 50 is generally illustrated in FIG. 4. The container 50 includes two outer walls 52 and 54 which are sealed together by a heat seal 56 about the periphery of the walls 52 and 54. The internal seal 58 divides the interior of the container 50 into a lower chamber 60 and an upper chamber 62.

The lower chamber 60 may include three ports 64, 66, and 68 in fluid communication with the lower chamber 60 as illustrated. While three ports are shown connected to the lower chamber 60, it should be understood that only two ports would be required for filling and administering a mixed solution from the container 50.

The upper chamber 62 includes a single port 70. The port 68 provides a means for filling the lower chamber 60, and the port 70 acts as a filling port for the upper chamber 62. The ports 68 and 70 may be located adjacent a flange 72 which is formed by a wider area of the walls 52 and 54 being heat sealed at the top portion of the container 50.

A frangible connector 74 is situated between a top portion of the lower chamber 16 and a bottom portion of the upper chamber 62. When the frangible connector 74 is broken, a valve 76 located within a plastic tube 78 of the frangible connector 74 allows fluid communication between the chambers 60 and 62.

Using the embodiment illustrated in FIGS. 4 and 5 for filling, mixing and administering one or more products to a patient, an additional port is provided than that described with reference to FIGS. 1–3 since both a fill port 68 and a drainage port 66 are provided for the lower chamber 60. The medication port 64 may optionally be included as desired for further addition of medication or supplemental administration.

In an embodiment of the present invention, the frangible seal is eccentric, i.e., located at one side. This provides, in some cases, improved mixing.

The containers 10 and 50 of the present invention are especially adapted for use in storing peritoneal dialysis solutions. A peritoneal dialysis solution usually includes as an osmotic agent dextrose or a similar compound. Similar to other medical solutions, it is known to sterilize peritoneal dialysis solutions with heat. Dextrose must be formulated at an acid pH (5–5.5) since dextrose caramelizes during sterilization at high pH.

However, it is desirable to maintain the other components of a peritoneal dialysis solution at a high pH. Thus, when the two solutions are mixed they are at a physiological pH. Therefore, it is known to store in two separate bags a peritoneal dialysis solution that is mixed when administered to the patient.

Pursuant to the present invention, the dextrose solution having a low pH can be filled in one of the chambers of the container 10 or 50. The other chamber can include the base portion of the peritoneal dialysis solution. The solutions can then be sterilized using heat. Following the post-sterilization, the two solutions can be mixed into the lower chamber of the container thereby raising the pH of the dextrose solution to a physiological acceptable pH of 6.5 to 7.4.

Accordingly, pursuant to the present invention, the dextrose formulation can be stored and sterilized at a low pH preventing caramelization. However, before being administered to the patient, the pH of the formulation can be brought to a physiological acceptable pH thereby reducing pain on infusion as well as reducing inhibition of polymorph phagocytosis and intracellular killing of bacteria.

By way of example, and not limitation, an example of a process for storing and sterilizing a peritoneal dialysis solution is as follows. The dextrose solution and base solution of a peritoneal dialysis solution are prepared separately. Electrolytes are distributed into the two separate solutions to achieve the best pH distribution. The dextrose and base solutions are placed in different compartments of the containers using the fill ports.

The container can now be sterilized without caramelization of the dextrose. After sterilization and prior to use, the connector is broken allowing mixing of the solutions.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A container for housing two products comprising:
a container defining an interior between a plurality of exterior sides including at least a base, a top end and two lateral sides connecting the base and the top end, the lateral sides having a length greater than the base or the top end;
means for dividing the interior into only a first chamber and a second chamber, the first chamber having a substantially larger volume than the second chamber wherein one of the chambers further includes an integrally formed neck portion extending along an entire length of the other one of the chambers;
a valve for providing selective communication between the first chamber and the second chamber;
a first port in fluid communication with the first chamber on one of the exterior sides of the container; and
a second port in fluid communication with the second chamber on the same one of the plurality of exterior sides of the container as the first port wherein the exterior side having the first port and the second port is neither of the two lateral sides.

2. The container of claim 1 wherein the valve includes a frangible member.

3. The container of claim 1 wherein the exterior side including the first port and the second port is at the base.

4. The container of claim 1 wherein the one of the plurality of exterior sides including the first port and the second port is at the top end.

5. The container of claim 1 wherein the second port is constructed and arranged to disperse mixed solutions.

6. The container of claim 1 further comprising a third port in fluid communication with one of the chambers.

7. The container of claim 1 wherein the second chamber has a larger volume than the first chamber.

8. A container having a plurality of exterior sides defining an interior including at least a base, a top end and two lateral sides connecting the base and the top end, the lateral sides having a length greater than at least one of the base and top end for filling and storing two products prior to mixing the products into a mixture, the container comprising:

a first chamber capable of holding a first product that enters the first chamber through a first port;

a second chamber in fluid communication with the first chamber capable of holding a second product that enters the second chamber through a second port, the first chamber having a substantially larger volume than the second chamber wherein one of the chambers further includes an integrally formed neck portion extending along an entire length of the other one of the chambers; and the first port and the second port located at the same exterior side of the container wherein the same exterior side having the first port and the second port is neither of the two lateral sides.

9. The container of claim 8 further comprising a container dividing seal between the first chamber and the second chamber.

10. The container of claim 8 further comprising a frangible connector between the first chamber and the second chamber.

11. The container of claim 8 further comprising an additional port in fluid communication with at least one of the chambers.

12. The container of claim 8 wherein the first port and the second port are at one of the plurality of exterior sides of the container wall at the base.

13. The container of claim 10 wherein the frangible connector is eccentric.

* * * * *